United States Patent [19]

Kleiner et al.

[11] Patent Number: 5,481,023

[45] Date of Patent: Jan. 2, 1996

[54] PROCESS FOR THE PREPARATION OF HYDROXYPHENYLCARBOXYLATES

[75] Inventors: Christoph Kleiner, Frick; Samuel Evans, Marly, both of Switzerland; Ralf Schmitt, Bensheim, Germany

[73] Assignee: Ciba-Geigy Corporation, Tarrytown, N.Y.

[21] Appl. No.: 129,789

[22] Filed: Sep. 30, 1993

Related U.S. Application Data

[63] Continuation of Ser. No. 958,890, Oct. 9, 1992, abandoned.

[30] Foreign Application Priority Data

Oct. 15, 1991 [CH] Switzerland .................. 3028/91

[51] Int. Cl.[6] .................................................. C07C 69/76
[52] U.S. Cl. ............................................................ 560/75
[58] Field of Search ............................................... 560/75

[56] References Cited

U.S. PATENT DOCUMENTS

| | | | |
|---|---|---|---|
| 3,330,859 | 7/1967 | Dexter et al. | 560/75 |
| 3,944,594 | 3/1976 | Kleiner et al. | 560/75 |
| 4,085,132 | 4/1978 | Park et al. | 560/75 |
| 4,112,240 | 9/1978 | Hulsmann et al. | 560/112 |
| 4,228,297 | 10/1980 | Haeberli et al. | 560/75 |
| 4,536,593 | 8/1985 | Orban et al. | 560/75 |
| 4,594,444 | 6/1986 | Orban | 560/75 |
| 4,618,700 | 10/1986 | Gubler et al. | 560/75 |
| 4,716,244 | 12/1987 | Orban | 560/75 |

FOREIGN PATENT DOCUMENTS 1490341  12/1967  France .

*Primary Examiner*—Paul J. Killos
*Attorney, Agent, or Firm*—Michele A. Kovaleski

[57] ABSTRACT

There is disclosed a process for the preparation of compounds of formula I

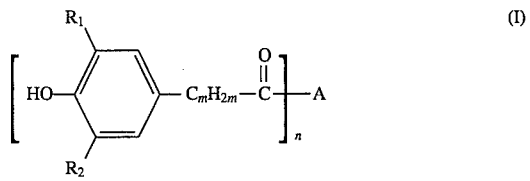

wherein $R_1$ and $R_2$ are each independently of the other $C_1$–$C_8$alkyl, m is 0, 1, 2 or 3, n is 1 or 2, and A, if n is 1, is $OR_3$, and $R_3$ is $C_4$–$C_{20}$alkyl or $C_5$–$C_{12}$cycloalkyl, or A, if n=2, has the formula —O—$C_xH_{2x}$—O— or —O—$(CH_2CH_2O)_aCH_2CH_2O$—, x is a number from 2 to 8 and a is a number from 1 to 12, by reacting a compound of formula II

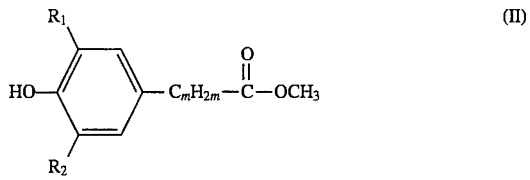

with a compound of formula III

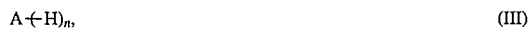

$$A(H)_n, \quad (III)$$

the reaction being carried out in the presence of an aluminium trialcoholate or triphenolate as catalyst.

12 Claims, No Drawings

PROCESS FOR THE PREPARATION OF HYDROXYPHENYLCARBOXYLATES

This is a continuation of application Ser. No. 07/958,890, filed on Oct. 9, 1992, now abandoned.

The present invention relates to a process for the preparation of hydroxyphenylcarboxylates and to the use of the catalysts employed.

The hydroxyphenylcarboxylates of formula I below are prepared by transesterification by a number of known processes (e.g. U.S. Pat. No. 3,330,859; U.S. Pat. No. 3,944,594; U.S. Pat. No. 4 085 132; U.S. Pat. No. 4,228,297; U.S. Pat. No. 4,536,593; U.S. Pat. No. 4,594,444; U.S. Pat. No. 4,618,700; U.S. Pat. No. 4,716,244). These processes are still not entirely satisfactory. Thus, for example, the titanium compounds used as catalysts are often difficult to separate from the reaction mass. Once consumed, they often have to be destroyed by troublesome procedures and arrangements must be made for disposal of the filtration residues. In particular, catalyst residues in the product can result in unwanted oxidation reactions which discolour the products.

There is therefore a need for novel, improved processes for preparing these compounds.

Aluminium alcoholates are already known as esterification and transesterification catalysts. They have been used, inter alia, for the preparation of ally β-phenylpropionates by transesterification (FR-A-1 490 341). These compounds are recommended for use as aromatic substances for the perfume industry.

Surprisingly, it has now been found that, by using aluminium alcoholates as catalysts, it is possible to obtain the hydroxycarboxylates described hereinafter cleanly, in good yield, without separation and oxidation problems, and with the aid of environmentally acceptable auxiliaries.

Accordingly, the invention provides a process for the preparation of compounds of formula I

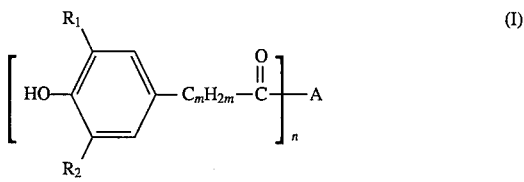

(I)

wherein $R_1$ and $R_2$ are each independently of the other $C_1$–$C_8$alkyl, m is 0, 1, 2 or 3, n is 1 or 2, and A, if n=1, is $OR_3$, and $R_3$ is $C_4$–$C_{20}$alkyl or $C_5$–$C_{12}$cycloalkyl, or A, if n=2, has the formula —O—$C_xH_{2x}$—O— or —O—($CH_2CH_2O$)$_a$ $CH_2CH_2O$—, x is a number from 2 to 8 and a is a number from 1 to 12, by reacting a compound of formula II

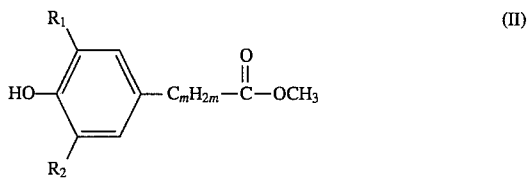

(II)

with a compound of formula III

A(H)$_n$, (III)

the reaction being carried out in the presence of an aluminium trialcoholate or triphenolate as catalyst.

$R_1$ and $R_2$ as $C_1$–$C_8$alkyl may be branched or unbranched radicals. Typical examples are methyl, ethyl, propyl, isopropyl, n-butyl, tsobutyl, tert-butyl, pentyl, isopentyl, hexyl, heptyl, 3-heptyl, octyl, 2-ethylbutyl, 1-ethylpentyl, 1,3-dimethylbutyl, 1,1,3,3-tetramethylbutyl, 1-methylhexyl, isoheptyl, 1-methylheptyl and 2-ethylhexyl. $R_3$ as $C_4$–$C_{20}$alkyl may be selected from members containing up to four carbon atoms in this list and, in addition, may be nonyl, decyl, undecyl, dodecyl, tridecyl, tetradecyl, pentadecyl, hexadecyl, heptadecyl, octadecyl, icosyl, 1,1,3-trimethylhexyl or 1-methylundecyl.

Preferably $R_1$ and $R_2$ are alkyl radicals of 1–4 carbon atoms. Typical examples will be found in the aforementioned list.

$R_3$ as $C_5$–$C_{12}$cycloalkyl may typically be cyclopentyl, cyclohexyl, cycloheptyl, cyclooctyl or cyclododecyl. Cyclopentyl and cyclohexyl are preferred, and cyclohexyl is most preferred.

$R_3$ is preferably higher alkyl, typically $C_8$–$C_{20}$alkyl, most preferably iso-octyl or n-octadecyl. Isooctyl will be taken to mean 2-ethylhexyl.

Preferably x is a number from 4 to 8 and a is a number from 1 to 4.

The process is preferably used for the preparation of compounds of formula I, wherein m is 2.

It is especially preferred to use the novel process for the preparation of compounds of formula I, wherein $R_1$ and $R_2$ are tert-butyl, $R_3$, if n=1, is n-octadecyl or isooctyl, and A, if n=2, is the group —O—($CH_2$)$_6$—O—.

Most preferably, the novel process is used for the preparation of compounds of formula I, wherein $R_1$ is methyl, $R_2$ is tert-butyl, n=2 and A is the group of formula —O—($CH_2CH_2O$)$_2CH_2CH_2O$—.

The inventive improvement of the process comprises the use of aluminium trialcoholates and triphenolates as catalysts. The invention therefore also relates to the use of aluminium trialcoholates and triphenolates as catalysts for the preparation of compounds of formula I by reacting compounds of formula II with compounds of formula III.

Suitable catalysts are compounds of formula IV

Al(OR)$_3$, (IV)

wherein R may be an aliphatic or aromatic radical.

Suitable aliphatic radicals are unsubstituted or OH-substituted $C_1$–$C_6$alkyl, preferably $C_1$–$C_4$alkyl.

An aromatic radical R has the formula

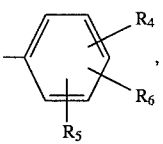

wherein $R_4$ and $R_5$ arc each independently of the other hydrogen or $C_1$–$C_4$alkyl, preferably methyl or tert-butyl, and $R_6$ is hydrogen or a group of formula

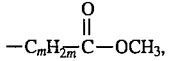

—$C_mH_{2m}$C—OCH$_3$, with the proviso that $R_6$, if different from hydrogen is in 4-position to the oxygen atom.

An aromatic radical R is preferably a radical of formula V

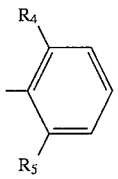

or is typically a radical of formula VI,

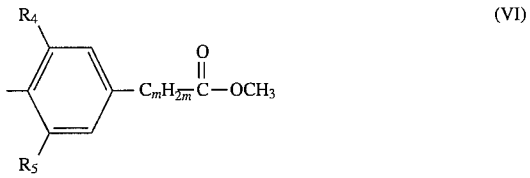

in which formula VI $R_4$ and $R_5$ are preferably different from hydrogen.

An aliphatic radical R is preferably methyl, ethyl, isopropyl or 2-hydroxybutyl, most preferably isopropyl.

It is especially advantageous to use a mixture of 65% of aluminium triisopropylate, 30% of petroleum spirit, 4% of isooctanol and 1% of isopropanol as catalyst formulation.

The novel process can be carried out in an inert organic solvent, typically in an aliphatic or aromatic hydrocarbon such as pentane, hexane, heptane, octane, cyclohexane, decaline, petroleum ether, or a mixture thereof, or benzene, toluene or xylene(s).

The reactants of formulae II and III are conveniently heated to form a homogeneous melt before the catalyst is added. They are preferably heated under reduced pressure (typically from 2 to 200 mbar, conveniently at 20 mbar) until a melt forms. This also serves to predry the reactants. The recommended temperature range therefor is conveniently 80°–90° C.

The catalyst is conveniently added to the reaction mixture in amounts of 0.05 to 10 mol %, preferably from 0.05 to 5 mol %, most preferably from 0.1 to 2 mol %, based on the compounds of formula II.

Customary operations such as stirring the reaction mixture are useful.

The reaction temperature is conveniently in the range from 120° to 200° C., preferably from 140° to 180° C., most preferably from 150° to 170° C.

The reaction time can vary over a wide range and is normally from 2 to 12 hours, depending on pressure and temperature.

The pressure during the reaction time is conveniently from 1 to 200 mbar, typically from 1 to 50 mbar, preferably from 1 to 15 mbar. As methanol is formed during the reaction, the pressure can change in the course of the reaction. For example, the pressure rises commensurately with the amount of methanol formed. If the methanol is removed, then it is expedient to reduce the pressure until any excess of component III is separated.

When the reaction is complete, any aluminium hydroxide resulting from aqueous impurities is expediently removed by filtration.

The catalyst is normally destroyed by acidifying the reaction mass with a suitable acid.

Suitable acids are typically acetic and formic acid or a mixture of both. A preferred embodiment of the process comprises using acetic acid, preferably in an at least 3-fold molar excess, based on the amount of catalyst, so as to react this latter to form aluminium acetate. A 3- to 6-fold excess, more particularly a 5-fold excess, is preferred. It is expedient to stir the reaction mixture for 30 minutes to 2 hours at 80°–110° C. with the acetic acid. If a solvent is used for the further working up, the bulk of the aluminium acetate remains in solution, whereas the product can be crystallised.

In a firther preferred embodiment of the inventive process, the catalyst is destroyed with formic acid which is added in at least 3-fold, and up to 20-fold, excess (based on $Al(^iPr)_3$. A 10-fold excess has been found useful. It is advantageous to stir the reaction mixture for ½ hour to 2 hours at 80°–100° C., preferably at 90° C., with formic acid. Upon standing, the two phases of the mixture separate. The lower, aqueous phase contains the formic acid and the aluminium salt and is substantially homogeneous, so that a separation of the organic phase containing the product is possible without difficulty.

When crystallising direct from the melt, the final product has an increased concentration of aluminium, but this usually poses no problems for the utility as stabiliser.

The product of formula I can thus either be crystallised direct by cooling and inoculating the reaction melt, or by taking up the reaction melt in a suitable solvent, cooling the solution and effecting crystallisation by inoculation. Suitable solvents are hydrocarbons such as pentane, hexane, heptane, octane, cyclohexane, decaline, petroleum ether or mixtures thereof; aromatic hydrocarbons such as benzene, toluene or xylene; alcohols and alcohol/water mixtures such as ethanol (80–100% ), methanol (80–100% ) and isopropanol (80–100%). Alcohol-water mixtures are preferred, especially methanol (80–100%).

Normally about equivalent amounts of the ester II and the alcohol III are used. The ratio of reactant II per equivalent of reactant III is conveniently from 0.8:1 to 1.3:1, preferably from 0.85:1 to 1.2:1.

Particular attention is drawn to the fact that, in the novel process, discolourations in the reaction mass and in the products are avoided. The discolouration problems referred to at the outset resulting from oxidation by catalyst residues are not encountered.

A further distinguishing feature of the process is that a filtration step is not absolutely necessary and that the number of by-products is gratifyingly low. Any catalyst residues in the final product do not interfere with the intended utility as stabiliser. If the product is crystallised from methanol, then the concentration of aluminium remaining in the final product is less than 10 ppm.

The compounds of formulae II, III and IV used in the novel process are known or can be prepared by known processes. Compounds of formulae II and III are described in the references cited at the outset.

The compounds of formula I obtained in the practice of this invention are used typically for protecting organic materials which are subject to thermal, oxidative and/or actinic degradation, including plastics materials and lubricants, and some are commercially available.

The invention is illustrated in more detail by the following non-limitative Examples in which parts and percentages are by weight, unless otherwise specificied.

EXAMPLE 1

Triethylene glycol bis[β-(3-tert-butyl-5-methyl-4-hydroxyphenyl)propionate (Compound of formula I, wherein $R_1$ is tert-butyl and $R_2$ is methyl, n and m are each 2 and A is the group of formula —O—$(CH_2CH_2O)_2CH_2CH_2O$—)

266 g of methyl β-(3-tert-butyl-5-methyl-4-hydroxyphenyl)propionate and 78 g of triethylene glycol are charged to a 1 liter sulfonation flask. The apparatus is closed, evacuated and the pressure is removed with nitrogen. Thereafter the contents of the flask are dried at 90° C./20 mbar for 1 hour. Then 1.46 g of aluminium triisopropylate are added and the apparatus is again evacuated to 3 mbar. The contents are heated for c. 1 hour to 160° C., while expelling methanol from c. 135° C. through the reflux condenser heated with warm water of 60° C. This methanol of reaction is condensed in a cooling trap, and about 36 g are obtained after a residence time of 8 hours. The pressure in the apparatus is thereafter removed with nitrogen and the reaction mass is stirred for 30 minutes with 6 ml of acetic acid at 100° C. The batch is filtered and the product is crystallised from 360 ml of 80% methanol, giving 282 g (90%) of a white powder which melts at 76°–79° C.

EXAMPLE 2

Stearyl β-(3,5-di-ten-butyl-4-hydroxyphenyl)propionate (Compound of formula I, wherein $R_1$ and $R_2$ are tert-butyl, n=1 and m=2, and A is —O—$^nC_{18}H_{37}$)

202 g of methyl β-(3,5-di-tert-butyl-4-hydroxyphenyl)propionate and 185 g of stearyl alcohol (dry) are charged to a reactor and fused at 80° C./200 mbar. When the reactants have fully melted, the vacuum is removed with nitrogen and 1.4 g of aluminium triisopropylate are added. The reactor is evacuated to 3 mbar and the contents are heated to 170° C. over 1 hour. The reaction melt is acidified with acetic acid and allowed to stand for crystallisation or taken up in methanol (97%) and crystallised. Yield: 95.5%; m.p. 53° C.

EXAMPLE 3

Hexanediol bis[β-(3,5-di-tert-butyl-4-hydroxyphenyl)propionate (Compound of formula I, wherein $R_1$ and $R_2$ are tert-butyl, n and m=2 and A is the groue —O—$(CH_2)_6$—O—)

320 g of methyl β-(3,5-di-tert-butyl-4-hydroxyphenyl)propionate ester and 64 g of hexanediol (dry) are charged to a reactor and fused at 80° C./200 mbar. When the reactants have fully melted, the vacuum is removed with nitrogen and 2.2 g of aluminium triisopropylate are added. The reactor is evacuated to 3 mbar and the contents are heated to 150° C. over 1 hour and stirred for 5 hours at this temperature. The reaction melt is acidified with acetic acid, taken up in methanol (97%) and crystallised after addition of 5% water. Yield: 90 %; m.p. 103°–108° C.

EXAMPLE 4

Isooctyl β-(3,5-di-ten-butyl,4-hydroxyphenyl)propionate (Compound of formula I, wherein $R_1$ and $R_2$ are tert-butyl, n=1 and m=2, and A is —O—$^iC_8H_{17}$)

393 g of methyl β-(3,5-di-ten-butyl-4-hydroxyphenyl)propionate and 201.1 g of anhydrous ($H_2O < 0.1\%$ by weight) isooctanol are charged to a reactor. The reaction mass is then fused, the temperature rising to 70° C. Then 4.5 g of aluminium triisopropylate are added as solid. The apparatus is closed, evacuated, and the pressure is removed with nitrogen. After addition of the catalyst, the reaction mass is heated to the reaction temperature of 150°–160° C. Methanol formed during the reaction is distilled from the reaction mass completely under increased vacuum (up to 20 mbar). A total amount of 43.1 g of methanol are collected in the distillation receiver. After a reaction time of c. 5 hours, excess isooctanol is distilled from the reaction mass almost completely under a gradually increased vacuum of 5 to 1 mbar and can be recycled without loss in quality. The residual reaction mass is cooled to 90° C. and acidified with 17 1.8 g of formic acid (6%), then stirred for half an hour at 90° C. and left to stand for phase separation for another half hour. The aqueous phase, which contains formic acid and aluminium salts, is substantially homogeneous and is separated from the organic phase that contains the product.

Aluminium salts remain in solution in the aqueous phase on account of the formic acid. The organic phase is thereafter washed twice with 170 g of water, distilled to dryness and filtered over a thermostatically controlled lens filter. Yield: 99.5%; $n_D^{20}$1.499.

What is claimed is:

1. A process for the preparation of a compound of formula I

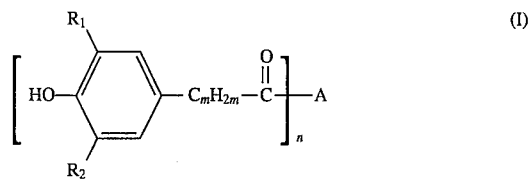

wherein $R_1$ and $R_2$ are each independently of the other $C_1$–$C_8$alkyl, m is 0, 1, 2 or 3, n is 1 or 2, and A, if n=1, is $OR_3$, and $R_3$ is $C_4$–$C_{20}$alkyl or $C_5$–$C_{12}$cycloalkyl, or A, if n=2, has the formula —O—$C_xH_{2x}$—O— or —O—$(CH_2CH_2O)_a$ $CH_2CH_2O$—, x is a number from 2 to 8 and a is a number from 1 to 12, by reacting a compound of formula II

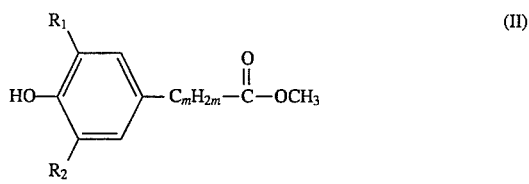

with a compound of formula III

the reaction being carded out in the presence of an aluminium trialcoholate or triphenolate as catalyst.

2. A process according to claim 1, wherein m is 2.

3. A process according to claim 1, wherein $R_1$ and $R_2$ are $C_1$–$C_4$alkyl.

4. A process according to claim 1, wherein $R_3$ is $C_8$–$C_{20}$alkyl, x is a number from 4 to 8 and a is a number from 1 to 4.

5. A process according to claim 2, wherein $R_1$ and $R_2$ are tert-butyl, $R_3$, if n=1, is n-octadecyl or isooctyl, and A, if n = 2, is the group —O—$(CH_2)_6$—O—.

6. A process according to claim 2, wherein $R_1$ is methyl and $R_2$ is tertobutyl, n=2 and A has the formula —O—$(CH_2CH_2O)_2CH_2CH_2O$—.

7. A process according to claim 1, which comprises the use of a catalyst of formula Al(OR)$_3$, wherein R is unsubstituted or OH-substituted $C_1$–$C_6$alkyl, or is a radical of formula

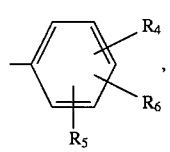

wherein $R_4$ and $R_5$ are each independently of the other hydrogen or $C_1$–$C_4$alkyl, and $R_6$ is hydrogen or a group of formula

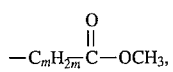

with the proviso that $R_6$, if different from hydrogen, is in 4-position to the oxygen atom.

8. A process according to claim 7, wherein R is unsubstituted or OH-substituted $C_1$–$C_6$alkyl.

9. A process according to claim 1, wherein the catalyst is aluminium triisopropylate.

10. A process according to claim 1, wherein the reaction is carded out in the temperature range from 120° to 200° C.

11. A process according to claim 1, wherein the pressure during the reaction is from 1 to 200 mbar.

12. A process according to claim 1, wherein after the reaction the catalyst is destroyed by addition of an acid, preferably acetic or formic acid.

* * * * *